United States Patent
Thatcher et al.

(10) Patent No.: US 9,629,940 B2
(45) Date of Patent: *Apr. 25, 2017

(54) BIOABSORBABLE POLYMERIC COMPOSITION FOR A MEDICAL DEVICE

(71) Applicant: OrbusNeich Medical, Inc., Fort Lauderdale, FL (US)

(72) Inventors: G. Lawrence Thatcher, Chelmsford, MA (US); Robert J. Cottone, Davie, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 345 days.

This patent is subject to a terminal disclaimer.

(21) Appl. No.: 14/542,716

(22) Filed: Nov. 17, 2014

(65) Prior Publication Data

US 2015/0073099 A1 Mar. 12, 2015

Related U.S. Application Data

(60) Continuation of application No. 13/370,394, filed on Feb. 10, 2012, now Pat. No. 9,173,973, which is a
(Continued)

(51) Int. Cl.
*A61L 27/26* (2006.01)
*A61L 27/18* (2006.01)
(Continued)

(52) U.S. Cl.
CPC ............... *A61L 27/26* (2013.01); *A61L 27/18* (2013.01); *A61L 27/58* (2013.01); *A61L 31/06* (2013.01);
(Continued)

(58) Field of Classification Search
None
See application file for complete search history.

(56) References Cited

U.S. PATENT DOCUMENTS 5,085,629 A 2/1992 Goldberg et al.
5,317,064 A 5/1994 Spinu
(Continued)

FOREIGN PATENT DOCUMENTS

EP 0401844 6/1990
EP 0600237 A1 6/1994
(Continued)

OTHER PUBLICATIONS

Yuancai Dong, Si-Shen Feng. Nanoparticles of poly(D,l-Lactide)/methoxy poly(ethylene glycol)-poly(D-L-lactide) blends for controlled release of paclitaxel. Journal of Biomedical Materials Research Part A. vol. 78A, Issue 1, pp. 12-19. Apr. 2006.
(Continued)

*Primary Examiner* — Robert A Wax
*Assistant Examiner* — Melissa Mercier
(74) *Attorney, Agent, or Firm* — Leason Ellis LLP

(57) ABSTRACT

A biodegradable and biocompatible nontoxic polymeric composition is provided which includes a base material such as a crystallizable polymer, copolymer, or terpolymer, and a copolymer or terpolymer additive. Medical devices manufactured from the composition are also provided.

2 Claims, 10 Drawing Sheets

Related U.S. Application Data continuation of application No. 12/508,442, filed on Jul. 23, 2009, now Pat. No. 8,137,603, which is a division of application No. 11/781,230, filed on Jul. 20, 2007, now Pat. No. 7,846,361.

(60) Provisional application No. 60/807,932, filed on Jul. 20, 2006, provisional application No. 60/862,433, filed on Oct. 20, 2006.

(51) Int. Cl.

| | | |
|---|---|---|
| A61L 31/06 | (2006.01) | |
| A61L 27/58 | (2006.01) | |
| B29C 47/00 | (2006.01) | |
| B29K 67/00 | (2006.01) | |
| B29K 105/00 | (2006.01) | |
| B29L 31/00 | (2006.01) | |

(52) U.S. Cl.
CPC .... *B29C 47/0066* (2013.01); *B29C 2793/009* (2013.01); *B29C 2793/0018* (2013.01); *B29K 2067/046* (2013.01); *B29K 2105/0085* (2013.01); *B29K 2995/006* (2013.01); *B29L 2031/7534* (2013.01); *C08L 2203/02* (2013.01); *C08L 2205/02* (2013.01); *Y10T 428/139* (2015.01); *Y10T 428/1352* (2015.01)

(56) References Cited

U.S. PATENT DOCUMENTS

| | | | |
|---|---|---|---|
| 5,320,624 A | 6/1994 | Kaplan et al. | |
| 5,531,998 A | 7/1996 | Mares et al. | |
| 5,700,901 A | 12/1997 | Hurst et al. | |
| 5,776,161 A | 7/1998 | Globerman | |
| 5,964,798 A | 10/1999 | Imran | |
| 6,001,395 A | 12/1999 | Coombes et al. | |
| 6,033,394 A | 3/2000 | Vidlund et al. | |
| 6,110,164 A | 8/2000 | Vidlund | |
| 6,245,103 B1 | 6/2001 | Stinson | |
| 6,251,134 B1 | 6/2001 | Alt et al. | |
| 6,254,632 B1 | 7/2001 | Wu et al. | |
| 6,258,382 B1 | 7/2001 | Takaoka et al. | |
| 6,312,458 B1 | 11/2001 | Golds | |
| 6,511,505 B2 | 1/2003 | Cox et al. | |
| 6,537,284 B1 | 3/2003 | Inoue | |
| 6,575,888 B2 | 6/2003 | Zamora | |
| 6,585,755 B2 | 7/2003 | Jackson et al. | |
| 6,599,314 B2 | 7/2003 | Mathis | |
| 6,607,548 B2* | 8/2003 | Pohjonen | A61L 27/26 606/105 |
| 6,652,575 B2 | 11/2003 | Wang et al. | |
| 6,652,579 B1 | 11/2003 | Cox et al. | |
| 6,730,116 B1 | 5/2004 | Wolinsky | |
| 6,770,729 B2 | 8/2004 | Van Antwerp | |
| 6,805,706 B2 | 10/2004 | Solovay et al. | |
| 6,896,697 B1 | 5/2005 | Yip et al. | |
| 7,070,607 B2 | 7/2006 | Murayama et al. | |
| 7,785,615 B2 | 8/2010 | Dave et al. | |
| 7,846,361 B2* | 12/2010 | Thatcher | A61L 27/18 264/148 |
| 7,897,224 B2* | 3/2011 | Thatcher | A61L 27/18 428/35.7 |
| 7,959,942 B2* | 6/2011 | Cottone | A61F 2/91 424/130.1 |
| 8,642,068 B2* | 2/2014 | Cottone | A61F 2/91 424/130.1 |
| 8,642,707 B2* | 2/2014 | Thatcher | A61L 27/18 525/415 |
| 8,691,321 B2 | 4/2014 | Cottone | |
| 2002/0007212 A1 | 1/2002 | Brown et al. | |
| 2002/0111671 A1 | 8/2002 | Stenzel | |
| 2004/0167572 A1 | 8/2004 | Roth et al. | |
| 2005/0107864 A1 | 5/2005 | Hong et al. | |
| 2006/0035854 A1 | 2/2006 | Goldstein et al. | |
| 2006/0041102 A1 | 2/2006 | Hossainy et al. | |
| 2006/0265048 A1 | 11/2006 | Cheng et al. | |
| 2015/0028513 A1 | 1/2015 | Cottone | |

FOREIGN PATENT DOCUMENTS

| | | |
|---|---|---|
| EP | 1065316 | 1/2001 |
| EP | 1737387 | 10/2005 |
| EP | 1681035 A1 | 7/2006 |
| WO | WO 9411441 | 5/1994 |
| WO | WO-9934750 | 7/1999 |

OTHER PUBLICATIONS

Dirk Wybe Grijpma, High Impact Strength Poly(Lactide) Tough Biodegradable Materials (Oct. 1, 1993) (Thesis, University of Groningen).

* cited by examiner

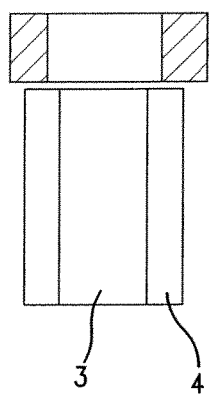 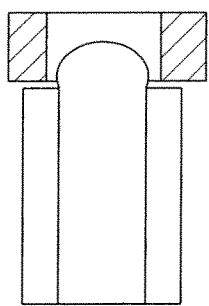 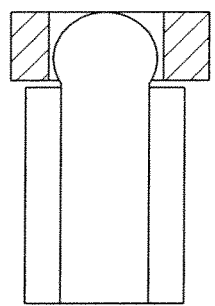 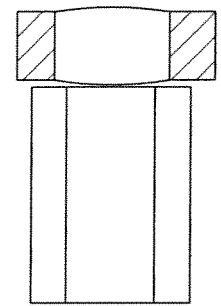
FIG. 3A     FIG. 3B     FIG. 3C     FIG. 3D
 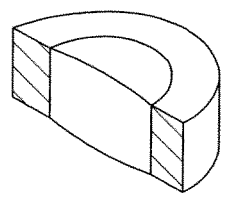 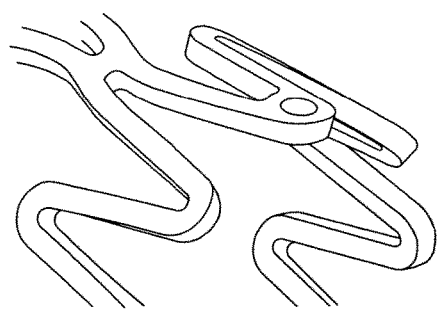
FIG. 3E     FIG. 3F     FIG. 3G

A-1

B-1

C-1

A-1-1

A-1-2

BIOABSORBABLE POLYMERIC COMPOSITION FOR A MEDICAL DEVICE

CROSS-REFERENCE TO RELATED APPLICATIONS

This application is a continuation of U.S. patent application Ser. No. 13/370,394, filed Feb. 10, 2012, which is a continuation of U.S. patent application Ser. No. 12/508,442, filed Jul. 23, 2009, now U.S. Pat. No. 8,137,603, which is a divisional of U.S. patent application Ser. No. 11/781,230, filed Jul. 20, 2007, now U.S. Pat. No. 7,846,361, which claims the benefit of and priority to U.S. Provisional Application Nos. 60/807,932, filed Jul. 20, 2006, and 60/862,433, filed Oct. 20, 2006.

All references cited in this specification, and their references, are incorporated by reference herein in their entirety where appropriate for teachings of additional or alternative details, features, and/or technical background.

FIELD OF INVENTION

Disclosed in the embodiments herein is a novel polymer composition, which includes a base material including a one or more bioabsorbable polymer, copolymer, or terpolymer, with a polymer or copolymer or terpolymer additive. In particular, the novel composition when used to fabricate implants allows for a "soft" breakdown mechanism allowing for the breakdown of the component polymers to be less injurious to the surrounding tissue.

BACKGROUND OF INVENTION

A persistent problem associated with the use of metallic stenting is found in the formation of scar tissue coating of the vascularly located stent, the so-called process of restenosis. Moreover, metallic or polymeric non-absorbable stents may prevent vascular lumen remodeling and expansion. Numerous approaches have been tried to prevent or heal tissue injury and reduce complement activation of the immune response. Furthermore, there is a need for a reduced inflammatory response and lower potential for trauma upon break-up of an implant and/or its component materials. A desirable improvement target may be found in the need for increased flexibility of shape and structure of medical devices for implantation, particularly into blood vessels.

Among the many commercially available bioabsorbable polymers are poly-alpha-esters (e.g., lactides (i.e., L-lactide and D,L-lactide)) and glycolides, polyester ethers (i.e. polydioxanone), and polycarbonates (i.e., glycolide or lactide-co-trimethylene carbonate), and tyrosine based polycarbonates. Many other bioabsorbable polymers are being developed for commercial use, particularly in different modes of drug delivery, which polymeric substances include polyethylene glycol-co-lactides, polyanhydides, polyorthoesters, polyester-amides or cyanoacrylates.

The present inventors have recognized a need to develop a compatible polymer blend for implants, such as stents and vascular synthetic grafts, which provide a toughening mechanism to the base polymer when the medical device is deployed in the body. They have hypothesized that the later may be performed by imparting additional molecular free volume to the base polymer to encourage sufficient molecular motion to allow for re-crystallization to occur at physiological conditions especially when additional molecular strain is imparted to the implant. They have theorized that increased molecular free volume can also increase the rate of water uptake adding both a plasticizing effect as well as increasing the bulk degradation kinetics.

REFERENCES

Reference is made to U.S. Pat. No. 6,607,548 B2 (Inion Ltd), issued Aug. 19, 2003, which discloses compositions are biocompatible and bioresorbable using a lactic acid or glycolic acid based polymer or copolymer blended with one or more copolymer additives. Implants made according to the '548 disclosure are said to be cold-bendable without crazing or cracking. Reference is also made to EP 0401844 which discloses a blend of poly-L-lactide with poly L-DL-lactide. Reference is also made to U.S. Pat. No. 5,317,064 disclosing polylactide stereocomplexing compositions.

SUMMARY

A novel polymer composition is provided that allows for a "soft" breakdown in vivo such that the breakdown proceeds while being friendly to the surrounding tissue (e.g., less inflammatory response, and rendering lower potential for trauma upon break-up of an implant). The polymer composition includes a base material such as a bioabsorbable polymer, copolymer, or terpolymer, which are selected for their ability to undergo hydrolytic and/or enzymatic degradation and absorption in vivo, and a copolymer or terpolymer additive.

Such novel polymer composition may comprise a polymer blend with the blend being optimized for enhanced hydrophilic property in order to reduce complement activation and minimize or prevent opsonization (see Dong and Feng, J of Biomedical Materials Research part A DOI 10.1002, 2006). To improve hydrophilicity, the novel polymer composition may be formulated to provide increased molecular free volume, allowing for increased uptake of water, and the rate of uptake of water, adding both a plasticizing effect as well as increasing the bulk degradation kinetics. Additional molecular free volume may also be used to encourage sufficient molecular motion so as to allow for re-crystallization to occur at physiological conditions, in particular when strain on the composition leads to additional molecular strain.

In an embodiment, there is provided a polymer/polymer blend implant comprising a biodegradable scaffold displaying flexibility for crimped fastening on a carrier system, as well as displaying elastic strut strength upon implantation into the body due to induction of crystallization if the polymer/polymer blend. The implant may comprise, for example, a tube-shaped expandable scaffold configured to fit within an organ space, such as the vasculature, including the cardiovasculatory system. Such a scaffold may achieve a combination of mechanical properties balancing elasticity, rigidity and flexibility.

In one embodiment the polymer composition and/or formulation, contains a polymer such as a poly(L-lactide), and/or a poly(D-lactide) as the base polymer, or copolymers thereof. In respect of copolymer compositions, the copolymers may be synthesized as block copolymers or as "blocky" random copolymers. The lactide chain length of copolymers may be selected to be sufficiently long enough to crystallize. Shortened degradation time, to provide, for example, enhanced degradation kinetics may be obtained by using a lower molecular weight composition and/or a base polymer that is more hydrophilic or suspect to hydrolytic chain scission.

Optionally included in such embodiment composition is modifying copolymers including, for example, poly L(or D)-lactide-co-tri-methylene-carbonate, or poly L(or D)-lactide-co-ε-caprolactone, which may be admixed to link the base polymers. In such copolymer-modifying copolymer embodiment, the composition may allow the development of a crystal morphology that can enhance the mechanical properties of the medical device, enhance processing conditions, and provide potential of cross-moiety crystallization, for example, strain induced thermal cross-links. The modifying polymer or co-polymer may also be used to affect enhanced degradation kinetics, such as with an ε-caprolactone copolymer moiety where the caprolactone remains amorphous with resulting segments more susceptible to hydrolysis.

In another embodiment composition the base copolymer includes L-lactide/D-lactide wherein one chain moiety is sufficiently long enough, and not sterically hindered, to crystallize with another lactide moiety. Optional co-moners with the base co-polymer include lesser sized moieties such as, for example, glycolide, polyethylene glycol (PEG), or monomethoxy-terminated PEG (PEG-MME).

In another embodiment, one may incorporate PEG copolymers, for example either AB di-block or ABA tri-block with the PEG moiety being approximately 1%, may be employed with maintenance of the mechanical properties of the lactide (see Enderlie and Buchholz SFB May 2006). Incorporation of either PEG or PEG-MME copolymers may also be used to facilitate drug attachment to the polymer, for example, in conjunction with a drug eluting medical device.

Embodiment hydrophilic compositions of the present invention are intended to allow for a "soft" or very gradual breakdown mechanism such that the breakdown proceeds while being friendly to the surrounding tissue (less inflammatory response, and rendering lower potential for trauma upon break up of an implant). Selecting a polymer or copolymer having an enhanced hydrophilic property for either the base polymer, or the additive, or both, the polymer blend may reduce complement activation and minimize or prevent opsonization.

In an embodiment composition, the polymers are selected to provide a racemate or stereocomplex crystal structure. For example, the copolymers may comprise a D-lactide and L-lactide, in a ratio sufficient to form a racemic crystal structure. A scaffold produced of such polymer compositions may provide enhanced mechanical properties through a molecular reorientation and crystallization effected during the radial strain of expansion from a crimped state to an expanded or implanted state. More specifically, a tubular stent scaffold of such embodiment may undergo racemate crystallization at the more tightly angled meandering struts after being crimped on to a carrier/implanting device, while still maintaining a substantially amorphous matrix elsewhere. When a tubular stent scaffold includes a hoop structure, the polymer may be fabricated so as to be capable of crystallization in the orthogonally expansion stretched ring or hoop structures during implantation generating strong resistance against collapse.

In another embodiment, cross-moiety crystallization is promoted between a base polyer, e.g., poly L-lactide or poly D-lactide, and a modifying copolymer with the same lactide segment, e.g., LPLA-TMC or DPLA-TMC respectively.

The composition of the polymer embodiments also may be modified for the particular functions assigned to a medical device. Thus, the polymer may contain fillers in the form of drugs or other pharmaceutical agents such as small molecule inhibitors of endogenous enzymes, radio-opaque markers (powders or other suitable particulates, and other factors.

The compositions of the present invention may include pharmacological agents such as tacrolimus, sirolimus, everolimus, prostacyclin, prostacyclin analogs, α-CGRP, α-CGRP analogs or α-CGRP receptor agonists; prazosin; monocyte chemoattactant protein-1 (MCP-1); immunosuppressant drugs such as rapamycin, drugs which inhibit smooth muscle cell migration and/or proliferation, anti-thrombotic drugs such as thrombin inhibitors, immunomodulators such as platelet factor 4 and CXC-chemokine; inhibitors of the CX3CR1 receptor family; antiinflammatory drugs, steroids such as dihydroepiandrosterone (DHEA), testosterone, estrogens such as 17β-estradiol; statins such as simvastatin and fluvastatin; PPAR-alpha ligands such as fenofibrate and other lipid-lowering drugs, PPAR-delta and PPAR-gamma agonists such as rosiglitazone; PPAR-dual-αγ agonists, LBM-642, nuclear factors such as NF-κβ, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angionesis inhibitor compound; peptides or antibodies which inhibit mature leukocyte adhesion, antibiotics/antimicrobials, and other substances such as tachykinins, neurokinins or sialokinins, tachykinin NK receptor agonists; PDGF receptor inhibitors such as MLN-518 and derivatives thereof, butyric acid and butyric acid derivatives puerarin, fibronectin, erythropoietin, darbepotin, serine proteinase-1 (SERP-1) and the like.

Included in embodiments of the present invention are devices made from such polymer compositions. Such devices include medical devices for implantation into a patient such as, without limitation, biodegradable, stents, stent grafts, vascular synthetic grafts, orthopedic devices, nerve guides, maxillofacial cranial devices, catheters, vascular shunts, or valves. Such devices may display bioabsorbable properties. Such implantation devices may include structure useful for inserting the implant into the body. For example, such implants may include snap-fit structure allowing for interaction between suitable parts of the medical device to allow the device to be held in a reduced size state which may aid in its insertion, and may aid its interaction with a carrier device used for its insertion (e.g., securing it on a carrier device without creep).

Embodiments of the invention are also directed to methods of making the biodegradable polymer compositions and methods for making the medical devices from the polymer compositions disclosed herein.

BRIEF DESCRIPTION OF THE DRAWINGS

FIGS. 3A-3G illustrate an embodiment method of radiopaque depot marking of a stent medical device: as seen in (a)-(d)) radiopaque material may be extruded into a cavity housed in the structure (g). As seen in cut-off views (e) and (f), such cavity may be a through-hole.

As illustrated in FIGS. 5A and 5B the radiopaque markers can be aligned in the structure to allow for easier identification upon imaging or use of other detection methods.

DETAILED DESCRIPTION

Figure 1:
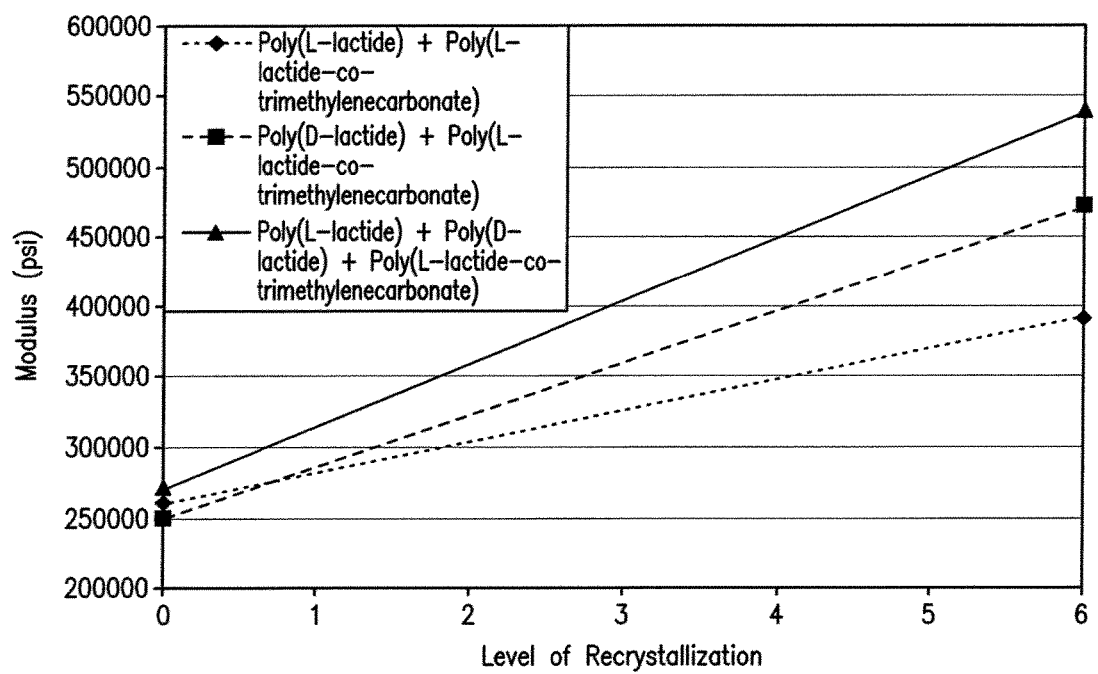
FIG. 1 depicts change in modulus with recrystallization of LPLA/LPLA/TMC non-racemate blend versus a DPLA/LPATMC with only cross moiety racemate and a DPLA/LPLA/LPLA-TMC with additional racemate formation.

In embodiments herein there are illustrated various compositions for bioabsorbable polymer blends, methods for making the compositions, and medical devices made of such bioabsorbable polymer blends.

The following nomenclature will now be used with the polymer nomenclature being based on the presence of the monomer type.

LPLA: Poly(L-lactide)
LPLA-PEG: Poly(poly-L-lactide-polyethylene glycol)
DPLA: Poly(D-lactide)
DPLA-TMC: Poly(poly D-lactide-co-trimethylene carbonate)
DLPLA: Poly(DL-lactide), a racemic copolymer D-co-L-lactide
LDPLA: Poly(L-co-D-lactide)
LDLPLA: Poly(L-co-DL-lactide), named for the method of monomer introduction
PGA: Poly(glycolide)
PDO: Poly(dioxanone) (PDS is Trademark)
SR: "Self reinforced" (a processing technique)
TMC: Trimethylene carbonate
PCL: Poly($\epsilon$-caprolactone)
LPLA-TMC: Poly(poly L-lactide-co-trimethylene carbonate)
LPLG: Poly(L-lactide-co-glycolide)
POE: Poly Orthoester In an embodiment of the present invention, the composition comprises a base polymer of poly(L-lactide) or poly(D-lactide). Advantageous base polymer compositions include blends of poly(L-lactide) and poly(D-lactide). Other advantageous base polymer compositions include poly(L-lactide-co-D,L-lactide) or poly(D-lactide-co-D,L-lactide) with a D,L-lactide co-monomer molar ratio from 10 to 30%, and poly(L-lactide-co-glycolide) or poly(D-lactide-co-glycolide) with a glycolide co-monomer molar ratio from 10 to 20%.

Another embodiment embodies a base polymer featuring a poly(L-lactide) moiety, and/or a poly(D-lactide) moiety, linked with a modifying copolymer thereof, including poly(L-lactide-co-tri-methylene-carbonate or poly(D-lactide-co-tri-methylene-carbonate) and (L-lactide-co-$\epsilon$-caprolactone), or poly(D-lactide-co-$\epsilon$-caprolactone), in the form of block copolymers or blocky random copolymers, wherein the lactide chain length is sufficient to affect cross-moiety crystallization.

In another embodiment, the polymer composition allows the development of the lactide racemate (stereo complex) crystal structure, between the L and D moieties, to further enhance the mechanical properties of the bioabsorbable polymer medical device. The formation of the racemate (stereo complex) crystal structure can accrue from formulations such as combinations of:

Poly L-lactide with Poly D-lactide with Poly L-lactide-co-TMC;
Poly D-lactide with Poly L-lactide-co-TMC;
Poly L-lactide with Poly D-lactide-co-TMC;
Poly L-lactide with Poly D-lactide with Poly D-lactide-co-TMC;
Poly L-lactide-co-PEG with Poly D-lactide-co-TMC; and
Poly D-lactide-co-PEG with Poly L-lactide-co-TMC.

Poly-lactide racemate compositions of this embodiment may have an especially advantageous characteristic in being "cold formable or bendable" without adding heat. Cold-bendable scaffolds of the invention do not require heating to become flexible enough to be crimped onto a carrier device or accommodate irregularly shaped organ spaces. Cold bendable ambient temperatures are defined as room temperature not exceeding 30° C. Cold-bendable scaffolds, for example, afford sufficient flexibility when implanted allowing for an expanded scaffold device in an organ space such as pulsating vascular lumen. For example, in terms of a stent, it may be desirable to utilize polymeric compositions that afford mostly amorphous polymer moieties after fabrication that can crystallize particularly when the secondary nested or end-positioned meandering struts when the scaffold is strained by stretching upon balloon expansion for implantation. Such cold-bendable polymeric scaffold embodiments of are not brittle and do not have to be preheated to a flexible state prior to implantation onto a contoured surface space in the body. Cold-bendability allows these blends to be crimped at room temperature without crazing, and moreover, the blends can be expanded at physiological conditions without crazing.

Poly-lactide racemate compositions and non-racemate compositions of embodiments herein may be processed to have blocky moieties allowing cross moiety crystallization even with the addition of an impact modifier to the blend composition. Such a blend introduces the possibility to design device specific polymer compositions or blends by producing either single or double Tg's (glass melt transition points).

Poly-lactide racemate compositions may show significant improvement in re-crystallization capability over, for example, non-racemate PLDL-lactide blends. An advantageous racemate alignment of the different polylactide moieties can be achieved, for example, by blending a poly-D-lactide with the copolymer poly L-lactide-co-TMC capable of forming racemate crystal across the different polylactide stereomoieties, for example, without limitation, when stretched during expansion to the required emplacement diameter. This strain induced crystallization, without adverse crazing, results in an increase of the mechanical properties reflected also in a positive change of modulus data over the base of the base materials.

Cross moiety crystallization of compositions with copolymers appears to be limited to copolymer with monomer molar ratios ranging from about 90:10 through 50:50. In fact, at a molar ratio of 50:50, the polymer moieties sterically impeded crystallization whereas the greater ratios are much more suitable for cross moiety crystallization. On the basis of experimental induced crystallization, different blends with various concentrations of lactide copolymers such as TMC or εCL, to which an excess of poly(D-lactide) for racemate alignment with the L-lactide component has been added, the effective concentration of the copolymer in a racemate composition may be equal to, or less than, 40%. Thus, the thermal cross-links formed by cross moiety crystallization serves to reduce elongation or creep while maintaining the intended toughening mechanism. The advantageously strong racemate composition affords increased modulus data in tensile tests avoiding the method for reducing the tensile strength in the polymer blend.

An advantageous racemate composition embodiment provides a bioabsorbable polymer with minimal degradation in terms of high residual monomer level such that the contaminant monomeric residual fraction does not exceed about 0.5%, or preferably not in excess of about 0.3%. In embodiment concentration of monomeric contaminant of the polymer of the present invention is as low as about 0.2%.

Polymer compositions of embodiments described herein may comprise a base polymer present from about 70% to 95% by weight, or from about 70% to 80% by weight of the composition. For example, in one embodiment, the polymer formulation may comprise from about 70% by weight poly L-lactide (about 2.5 to 3 IV) with the poly L-lactide-co-TMC (70/30 mole/mole) (1.4 to 1.6 IV). In another embodiment, the polymer formulation may comprise 70% by weight triblock poly L-lactide-co-PEG (99/01 mole/mole) (2.5 to 3 IV) with the poly L-lactide-co-TMC (70/30 mole/mole) (1.4 to 1.6 IV). Furthermore, the polymer composition may comprise a formulation of about 70% by weight diblock poly L-lactide-co-PEG-MME (95/05 mole/mole) (2.5 to 3 IV) with poly L-lactide-co-TMC (70/30 mole/mole) (1.4 to 1.6 IV). Other embodiments provide formulations wherein ε-caprolactone is substituted in a composition for the aforementioned TMC. Similarly, an embodiment may provide formulations wherein PEG-MME may be substituted for PEG.

As is understood in this art, polymer compositions of the present invention can be customized to accommodate various requirements of the selected medical device. The requirements include mechanical strength, elasticity, flexibility, resilience, and rate of degradation under physiological and localized anatomical conditions. Additional effects of a specific composition concern solubility of metabolites, hydrophilicity and uptake of water and any release rates of matrix attached or enclosed pharmaceuticals.

The polymer implant utility can be evaluated by measuring mass loss, decrease in molecular weight, retention of mechanical properties, and/or tissue reaction. More critical for scaffold performance are hydrolytic stability, thermal transitions crystallinity and orientation. Other determinants negatively affecting scaffold performance include, but not exclusively, monomeric impurities, cyclic and acyclic oligomers, structural defects and aging.

The medical device fashioned from the polymer compositions above may be significantly amorphous post extrusion or molding. Such devices may be subjected to controlled re-crystallization to induce incremental amounts of crystallinity and mechanical strength enhancement. Further crystallization can be induced by strain introduction at the time of device deployment. Such incremental re-crystallization may be employed either on a device "blank" prior to secondary or final fabrication (such as by laser cutting) or post such secondary fabrication. Crystallization (and thus mechanical properties) can also be maximized by strain induction such as by "cold" drawing polymeric tubing, hollow fiber, sheet or film, or monofilament prior to further fabrication. Crystallinity has been observed to contribute a greater stiffness in the medical device. Therefore, the polymer composition and steric complex of the scaffold has both amorphous and paracrystalline moieties. The initially semicrystalline polymer portion can be manipulated by the action of stretching or expansion of a given device. Yet an adequate amount of amorphous polymeric character is desirable for flexibility and elasticity of the polymeric device. The usual monomer components include lactide, glycolide, caprolactone, dioxanone, and trimethylene carbonate.

In one embodiment, the medical device manufactured from such composition is a scaffold strut structure for implantation into the body, for example, a stent. These structures are to be crimpable so as to be tightened around and thereby fastened on a carrier device. Conversely, the same scaffold is expandable without stress crazing or cracking. The mechanical properties of a stent biodegradable scaffold implant requires strength, elasticity and flexibility to cope with the fluctuating pulse compression of the surrounding tissue without dislocation and injurious impact at the implantation site throughout the desirable gradual process of biological degradation and absorption of the scaffold struts. Therefore, these properties have to be build into the scaffold polymer content and structure in terms of certain criteria. The stent should have polymeric properties are amenable to expansion by means of a thermally enhanced or non-thermal balloon. The polymeric embodiment provides the ability to orient and/or crystallize in scaffold struts upon orthogonal strain of deployment, by e.g. balloon dilation. Thus, the crystallization effect provides improved mechanical properties such as hoop strength, as in compression resistance, elastic recoil, and polymer stability. The stent may also be constructed to allow relatively uniform exposure to local tissue or circulatory bioactive factors and enzymes perfusing and acting on the polymer structure during bioabsorption.

Advantageously, the rate of in situ breakdown kinetics of the polymeric matrix of an organ space implant, such as a cardiovascular stent, is sufficiently gradual to avoid tissue overload, inflammatory reactions or other more adverse consequences. In an embodiment, the scaffold is fabricated to survive at least one month.

As shown in the following examples, the comparative degree of amorphous and crystalline properties can be designed into the polymer. Thus, L-lactic polymers are found to yield a semicrystalline morphology, while the racemic poly(D,L-lactic) results in an amorphous polymer. A poly(L-glycolide) is semicrystalline. The following examples show a process for fabricating bioabsorbable scaffold PLDL-lactide blends.

Example 1

A test disk was injection molded from a composition of a racemic mixture of poly(L-lactide) and poly(D-lactide) with 15% by weight copolymer modifier of a 50:50 molar ratio poly(L-lactide-co-TMC). Injection cylinder temperatures were between 110° C. and 225° C. with a mold temperature of 50° F. to 82° F., to mold an amorphous disk. Injection pressure was set between 1300 and 1450 psi with a 50 second cycle time. It was found that an adequate degree of crystallinity could be produced in the polymer. DSC analysis confirmed the formation of both the conventional lactide crystal and the racemate crystal morphology.

Example 2

The polymer mixture is blend extruded into a narrow tube, and a scaffold form may be cut with a laser under a microscope to produce a cage-like mesh device of meandering struts connected to hoop-like rings positioned at one end and/or at the middle portion of the device. The resulting scaffold device includes a primary meandering scaffold forming a circumferential mesh structure containing a pattern of secondary meandering struts nested within the scaffold as well as at or near the ends of the scaffold. The second meandering struts may be shaped to form upon full implant expansion, a less sinusoidal or more straight hoop or ring shape than the first meandering struts, in orthogonal direction to the longitudinal axis of the tubal device. The expanded second meandering struts having smaller or shorter meandering loops or curves are stretched further during expansion. These struts may form thus hoops of greater crystallinity and therefore greater rigidity with elasticity so that the implant is resistant against creeping change or dislocation.

Example 3

The polymer compositions may be prepared from commercially available granular materials and copolymer additives. The dry components are weighed according to the desired weight ratio into a container rotating in a suitable for 30 minutes or until a homogenous mixture is obtained followed by further drying in vacuo at 60° C. for 8-12 hours or overnight. As described above, the thoroughly mixed components may be melt blended and injection molded into a pair of matching plates. The composition rendering polymer sheets exhibiting a suitable elasticity and an appearance of amorphous morphology or very low degree of crystallinity under a polarizing light source may be extruded with a back pressure of 40-50 bar under melting temperature of 120-160° C. while being homogenized with a 28 blade screw at 40-80 rpm The extruder melt blending and homogenization conditions of the material during metering phase of the process may include a screw speed of 60-100 rpm. The relatively mild injection molding process may use an exit temperature of 120° C.-150° C., at a velocity of 80-300 mm/s, a maximum injection pressure of 2500 bar, a pack pressure of 1000-2300 bar for 3 to 8 seconds, into mold kept at room temperature. The total cycle time may be one minute or less from injection to ejection from the mold plate.

Example 4

Dry polymer racemate mixture of poly(D-lactide) and poly(L-lactide-co-TMC) was blended at a weight ratio of 70:30 and processed with a single melt-extrusion step at 185-225° C. into a tube-shaped amorphous bioabsorbable racemate capable polymer blend. The instant method of melt-extrusion minimized polymer degradation due to excessive exposure to heat and shear. Subsequent testing showed effective induction of crystallization and development of the racemate crystal morphology. Such racemate copolymer hybrids have been found to confirm effective cross moiety crystallization. Moreover, racemate material can be created to have multiple transition temperatures indicating polymorphic and or pleomorphic structures. Thus, it has been found that the instant polymer scaffold was sufficiently flexible to be crimped onto a rubber bulb carrier, but for deployment in tissue the polymer moiety strength may be increased proportionally to expansion strain.

Example 5

Dry poly(L-lactide) with a racemic excess of poly(D-lactide) were blended with 30% by weight poly(L-lactide-co-TMC) under dry nitrogen, followed by melt blending and extrusion followed by rapid air quenching. Subsequent re-crystallization and testing confirmed significantly more racemate formation and increase in modulus over the formulation of example 4.

Synthesis is influenced by several distinct factors affecting the mechanical performance of the bioabsorbable polymer suitable for an implantable structure, such as monomer selection, initiator selection, polymerization conditions, and presence of additives or residuals. Furthermore, polymeric properties that determine the effectiveness of the implant include hydrophilicity, crystallinity, melt and glass transition temperatures, molecular weight, molecular weight distribution, end groups, sequence distribution i.e., random vs. blocky), presence of residual monomer or additives, and stability during conversion.

In one embodiment, pharmaceutical compositions may be incorporated within the polymers by, for example, grafting to the polymer active sites, or coating. An embodiment of the polymer according to the invention affords attachment or incorporation the biological healing factors or other drugs in the polymeric matrix or a polymer coating.

In another embodiment, the composition may be constructed to structurally enclose or attach to drugs in the polymeric matrix. The purpose of such additives may to provide, for example with respect to a stent, treatment of the cardiovascular system or in vascular site in contact with the medical device polymer. The kind of enclosure or attachment of drugs in the polymer may determine the rate of release form the device. For example, the drug or other additive may be bound in the polymer matrix by various known methods including but not limited to covalent bonds, non-polar bonds as well as an ester or similar bioreversible bonding means.

Embodiments of the bioabsorbable polymeric scaffold of an implantable configuration are known as useful for drug delivery. Therefore as described below, an extensive variety of compounds are possible agents to treat or modify the affected tissue at the locus of implantation as well as possibly further as e.g. in the entire cardiovascular system or other affected organs.

Examples of compounds or pharmaceutical compositions which can be incorporated in the matrix, and/or impregnated into the medical device include, but are not limited to tacrolimus, sirolimus, everoolimus, prostacyclin, prostacyclin analogs, α-CGRP, α-CGRP analogs or α-CGRP receptor agonists; prazosin; monocyte chemoattactant protein-1 (MCP-1); immunosuppressant drugs such as rapamycin, drugs which inhibit smooth muscle cell migration and/or proliferation, antithrombotic drugs such as thrombin inhibitors, immunomodulators such as platelet factor 4 and CXC-chemokine; inhibitors of the CX3CR1 receptor family; antiinflammatory drugs, steroids such as dihydroepiandrosterone (DHEA), testosterone, estrogens such as 17β-estradiol; statins such as simvastatin and fluvastatin; PPAR-alpha ligands such as fenofibrate and other lipid-lowering drugs, PPAR-delta and PPAR-gamma agonists such as rosiglitazone; PPAR-dual-αγ agonists, LBM-642, nuclear factors such as NF-κβ, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angionesis inhibitor compound; peptides or antibodies which inhibit mature leukocyte adhesion, antibioticsiantimicrobials, and other substances such as tachykinins, neurokinins or sialokinins, tachykinin NK receptor agonists; PDGF receptor inhibitors such as MLN-518 and derivatives thereof, butyric acid and butyric acid derivatives puerarin, fibronectin, erythropoietin, darbepotin, serine proteinase-1 (SERP-1) and the like. The aforementioned compounds and pharmaceutical substances can be applied to the scaffold of the device alone or in combinations and/or mixtures thereof. Moreover, the polymer attached or enclosed drug material can be bound covalently or ionically to the polymeric moieties as well as entrapped physically in the polymeric matrix. Wherever suitable the drug may be present in the form ester-type cross-links, microparticles, or micelle clusters.

In one embodiment, a bioabsorbable implantable medical device be covered with a biodegradable and bioabsorbable coating containing one or more barrier layers where the polymer matrix contains one or more of the aforementioned pharmaceutical substances. In this embodiment, the barrier layer may comprise a suitable biodegradable material, including but not limited to, suitable biodegradable polymers including: polyesters such as PLA, PGA, PLGA, PPF, PCL, PCC, TMC and any copolymer of these; polycarboxylic acid, polyanhydrides including maleic anhydride polymers; polyorthoesters; poly-amino acids; polyethylene oxide; polyphosphacenes; polylactic acid, polyglycolic acid and copolymers and mixtures thereof such as poly(L-lactic acid) (PLLA), poly(D,L-lactide), poly(lactic acid-co-glycolic acid), 50/50 (DL-lactide-co-glycolide); polydixanone; polypropylene fumarate; polydepsipeptides; polycaprolactone and co-polymers and mixtures thereof such as poly(D, L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate. The number of barrier layers that the polymeric scaffold on a device may have depends on the amount of therapeutic need as dictated by the therapy required by the patient. For example, the longer the treatment, the more therapeutic substance required over a period of time, the more barrier layers to provide the pharmaceutical substance in a timely manner.

In another embodiment, the additive in the polymer composition may be in the form of a multiple component pharmaceutical composition within the matrix such as containing a fast release pharmaceutical agent to retard early neointimal hyperplasia/smooth muscle cell migration and proliferation, and a secondary biostable matrix that releases a long acting agent for maintaining vessel patency or a positive blood vessel remodeling agent, such as endothelial nitric oxide synthase (eNOS), nitric oxide donors and derivatives such as aspirin or derivatives thereof, nitric oxide producing hydrogels, PPAR agonist such as PPAR-α ligands, tissue plasminogen activator, statins such as atorvastatin, erythropoietin, darbepotin, serine proteinase-1 (SERP-1) and pravastatin, steroids, and/or antibiotics.

In another embodiment, there is provided a method for treating vascular disease such as restenosis and atherosclerosis, comprising administering a pharmaceutical substance locally to a patient in need of such substance. The method comprises implanting into a vessel or hollowed organ of a patient a medical device of the present invention with a coating, which coating comprises a pharmaceutical composition comprising a drug or substance for inhibiting or slowing smooth muscle cell migration and thereby restenosis, and a biocompatible, biodegradable, bioerodable, nontoxic polymer or non-polymer matrix, wherein the pharmaceutical composition comprises a slow or controlled-release formulation for the delayed release of the drug. The coating on the medical device can also comprise a ligand such as an antibody for capturing cells such as endothelial cells and or progenitor cells on the luminal surface of the device so that a functional endothelium is formed.

The medical devices which may be made from the compositions of the present disclosure may comprise any medical device for implantation including, without limitation, stents, grafts, stent grafts, synthetic vascular grafts, shunts, catheters, and the like. The medical device embodiments of the present invention may provide a drug delivery system that features different gradual release rates of a drug or a mixture of drugs for effective treatment of the implant site in a tissue or organ structure. Such devices may also include in the composition, or in the structure composed of the composition, radiopaque substances for enhancing traceability of the medical device in situ. Such radiopaque substances may include nontoxic materials which would interfere with the intended healing process.

The medical devices of the invention can be structurally configured to provide the ability to change and conform to the area of implantation to allow for the normal reestablishment of local tissues. The medical devices can transition from solid to a "rubbery state" allowing for easier surgical intervention, than, for example, a stainless steel stent. Moreover, the rubbery state of the device offers less risk of any injurious encounters with the vascular walls in the event of a removal from a vascular location.

In embodiments disclosed herein, the medical device comprises a stent, which is structurally configured to be deployed into, for example, an artery or a vein, and be able to expand in situ, and conform to the blood vessel lumen to reestablish blood vessel continuity at the site of injury. The stent can be configured to have many different arrangements so that it is crimpable when loading and expandable and flexible at physiological conditions once deployed. Various embodiments of biodegradable polymeric stents, and/or stent walls with different configuration may be envisioned, as are illustrated in co-pending patent applications. For example, the stent is a tubular structure comprising struts operably designed to allow blood to traverse its walls so that the adjacent tissues are bathed or come in contact with it as blood flows through the area. The particular stent design depends on the size of the stent radially and longitudinally.

In respect of stents, the composition of the polymer may be designed to afford a combination of rigidity, elasticity, and flexibility such that the in situ effect of the stent results in effective luminal support for healing and drug treatment of the cardio-vascular system. With respect to stents, in particular, the composition of the polymers may be adjusted and selected such that it affords sufficient polymer strength to resist fluctuating vascular compression forces and blood flow rates. This structural and flexural strength is designed to persist during in situ bio-erosion of polymeric material which may extend over many days, or a few months. This residual strength of the polymer can be measurably monitored for at least enough time before a collapse of the treated vessel and keep the healing process on track. A composition for a stent may be designed to provide transitions gradually from the initial rigidly buttressing character within a vascular location to a rubber-like or "rubbery" consistency capable of maintaining a clinical function, such as preventing restenosis. The polymer composition may further be selected to offer smooth polymerized surfaces both proximal and distal to vascularly engaged regions so as to minimize tissue irritation or injury and thus not to evoke a clinically significant immune response. The polymer may be selected so as to allow a balloon driven expansion. Such an expandable medical device would comprise a thermal balloon or non-thermal balloon wherein the medical device can have a structure which is crimpable during loading and expandable without stress crazing in physiological conditions. Advantageously, the polymer composition may be selected to orient and/or crystallize upon strain of deployment, for example during balloon dilation, in order to improve its mechanical properties.

By careful selection of polymer compositions and structural construct of the medical device, immunogenicity and inflammatory responses can be minimalized. For example, if the device is shaped to lack protruding contours there may be precluded, or at least minimalized, polymeric and structural antigenicity so as to slow an immune response. Similarly, by selecting appropriate copolymers in the appropriate ratio, the resulting breakdown products of the polymers comprising a medical device may be more "friendly," or less irritating or immunogenic, to the host, such as, for example, the vascular wall. When the polymer composition is designed to elicit slow breakdown kinetics, tissue overload or other inflammatory responses at the site of implantation may be avoided.

Further disclosed herein is a method for making a bioabsorbable medical device of the present invention comprising: blending a crystallizable composition comprising a base polymer of poly L-lactide or poly D-lactide linked with modifying copolymers comprising poly L(or D)-lactide-co-Tri-methylene-carbonate or poly L(or D)-lactide-co-ε-caprolactone in the form of block copolymers or as blocky random copolymers wherein the lactide chain length is sufficiently long enough to allow cross-moiety crystallization; molding the polymer composition to structurally configure said implant; and cutting the implant to form desired patterns.

Another method for fabricating a medical device of the present application comprises: preparing a biodegradable polymeric structure; designing said polymeric structure to be configured to allow for implantation into a patient; cutting said structure into patterns configured to permit traversing of the device through openings and to allow for crimping of the device (as described in co-pending patent application Ser. No. 11/781,225, filed concurrent herewith). Embodiments utilizing secondary meandering struts which are expanded to the crystallized hoop form (as described in co-pending patent application Ser. No. 11/781,225, filed concurrent herewith) are particularly useful in securing the scaffold implant in the organ space as the crystalline moiety is less rapidly degraded and bioabsorbed and therefore advantageously capable of maintaining position and integrity of the scaffold, thus preventing premature collapse and dangerous bulk break-up of the scaffold.

As is well understood in the art, the polymeric scaffolds of the above described embodiments may lack contrast to be detected by the currently available detection devices such as x-ray monitors. Therefore, the contrast detection enhancement of tissue implants by electron-dense or x-ray refractile markers is advantageous. Such markers can be found in biodegradable spot depots filled with radiopaque compositions prepared from materials known to refract x-radiation so as to become visible in photographic images (FIGS. 3-7). Suitable materials include without limit, 10-90% of radiopaque compounds or microparticles which can be embedded in biodegradable moieties, particularly in the form of paste like compositions deposited in a plurality of cup shaped receptacles located in preformed polymeric scaffold strut elements.

The radiopaque compounds can be selected from x-radiation dense or refractile compounds such as metal particles or salts. Suitable marker metals may include iron, gold, colloidal silver, zinc, magnesium, either in pure form or as organic compounds. Other radiopaque material is tantalum, tungsten, platinum/iridium, or platinum. The radiopaque marker may be constituted with a binding agent of one or more aforementioned biodegradable polymer, such as PLLA, PDLA, PLGA, PEG, etc. To achieve proper blend of marker material a solvent system is includes two or more acetone, toluene, methylbenzene, DMSO, etc. In addition, the marker depot can be utilized for an anti-inflammatory drug selected from families such as PPAR agonists, steroids, mTOR inhibitors, Calcineurin inhibitors, etc.

In one embodiment comprising a radioopaque marker, iron containing compounds or iron particles encapsulated in a PLA polymer matrix to produce a pasty substance which can be injected or otherwise deposited in the suitably hollow receptacle contained in the polymeric strut element. Such cup-like receptacles are dimensioned to within the width of a scaffold strut element. Heavy metal and heavy earth elements are useful in variety of compounds such as ferrous salts, organic iodine substances, bismuth or barium salts, etc. Further embodiments that may be utilized may encompass natural encapsulated iron particles such as ferritin that may be further cross-linked by cross-linking agents. Furthermore, ferritin gel can be constituted by cross-linking with low concentrations (0.1-2%) of glutaraldehyde.

The radioopaque marker may be applied and held in association with the polymer in a number of manners. For example, the fluid or paste mixture of the marker may be filled in a syringe and slowly injected into a preformed cavity or cup-like depression in a biodegradable stent strut through as needle tip. The solvents contained in the fluid mixture can bond the marker material to the cavity walls. The stent containing radiopaque marker dots can be dried under heat/vacuo. After implantation, the biodegradable binding agent can breakdown to simple molecules which are absorbed/discharged by the body. Thus the radiopaque material will become dispersed in a region near where first implanted.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Figure 2A:
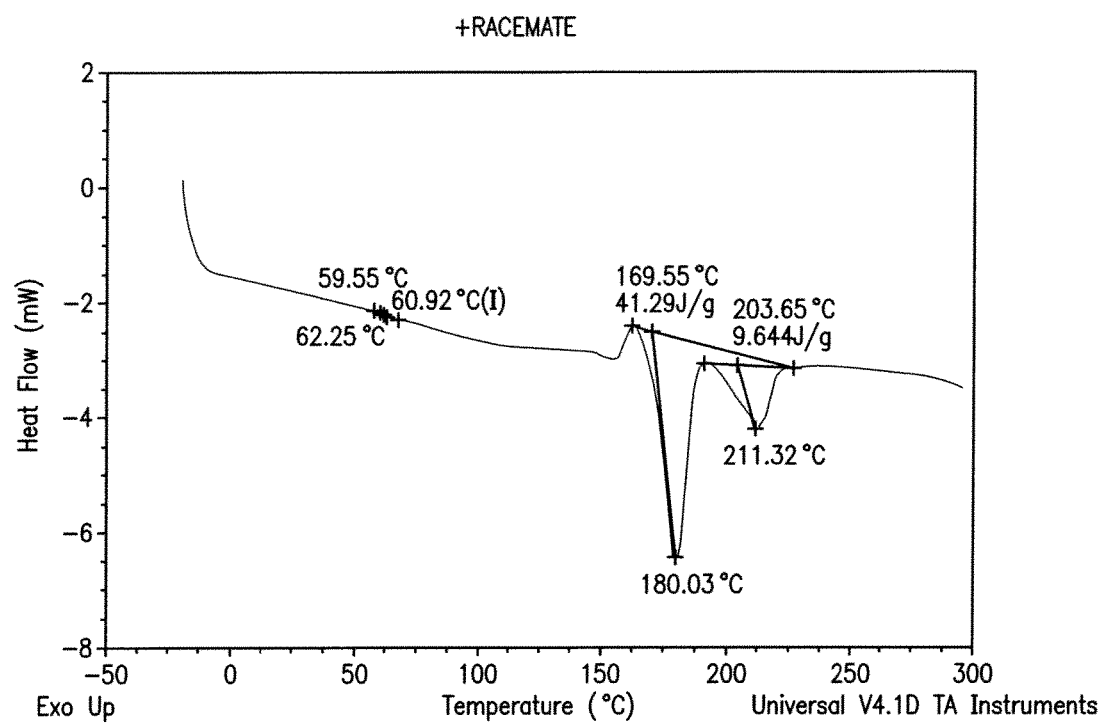
FIG. 2A and FIG. 2B depict DSC curves of polymer with racemate and without racemate formation, respectively: as illustrated racemate melt is shown to be significantly different in profile for the +racemate vs. the −racemate.
Figure 2B:
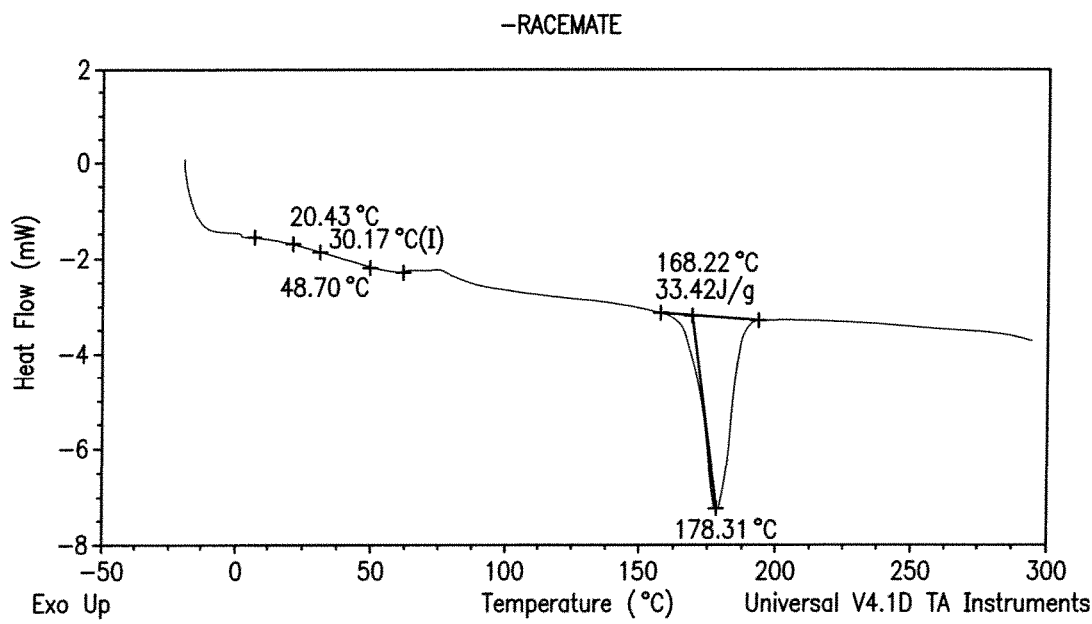

Now turning to the remaining figures:

FIG. 1 depicts change in modulus with recrystallization of LPLA/LPLA/TMC non-racemate blend versus a DPLA/LPA/TMC with only cross moiety racemate and a DPLA/LPLA/LPLA-TMC with additional racemate formation;

FIG. 2A and FIG. 2B depict DSC curves of polymer with racemate and without racemate formation, respectively: as illustrated racemate melt is shown to be significantly different in profile for the +racemate vs. the −racemate.

FIGS. 3A-3G illustrate an embodiment method of radiopaque depot marking of a stent medical device: as seen in (a)-(d)) radiopaque material may be extruded into a cavity housed in the structure (g). As seen in cut-off views (e) and (f), such cavity may be a through-hole.

Figure 4A:
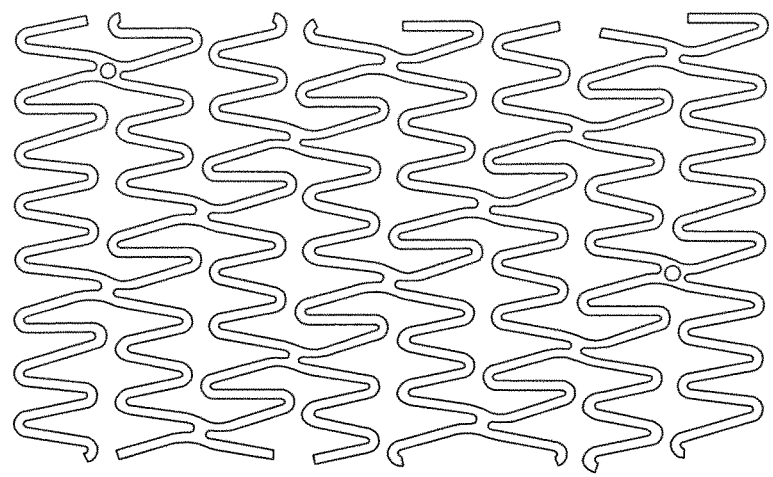
FIGS. 4A-4C illustrates different stent patterns of s scaffold with radiopague markers. As illustrated, the radiopaque markers can be placed at different locations on the stent patterns, while still allowing detection using radiopaque detection means.
Figure 4B:
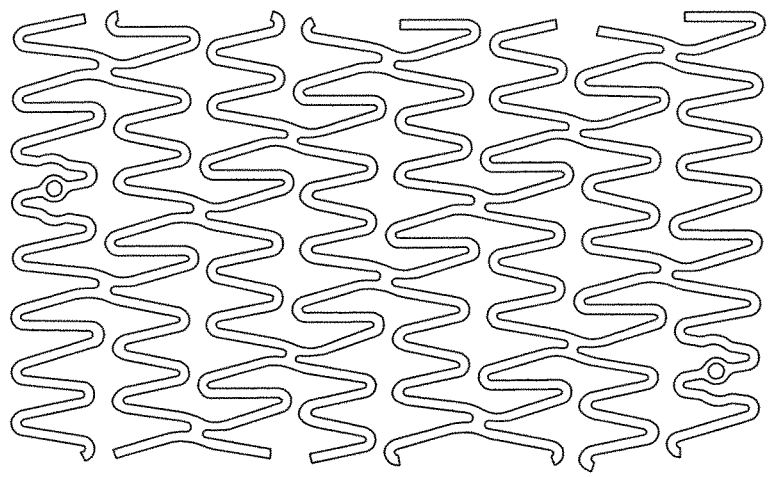
Figure 4C:
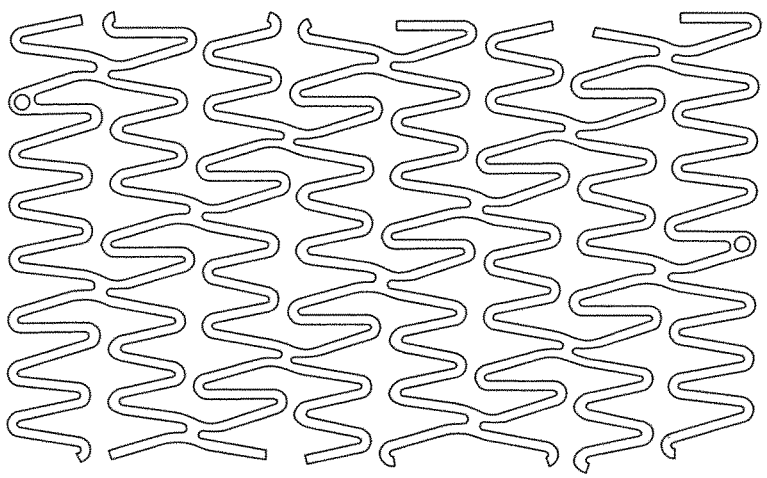

FIGS. 4A-4C illustrates different stent patterns of s scaffold with radiopague markers. As illustrated, the radiopaque markers can be placed at different locations on the stent patterns, while still allowing detection using radiopaque detection means.

Figure 5A:
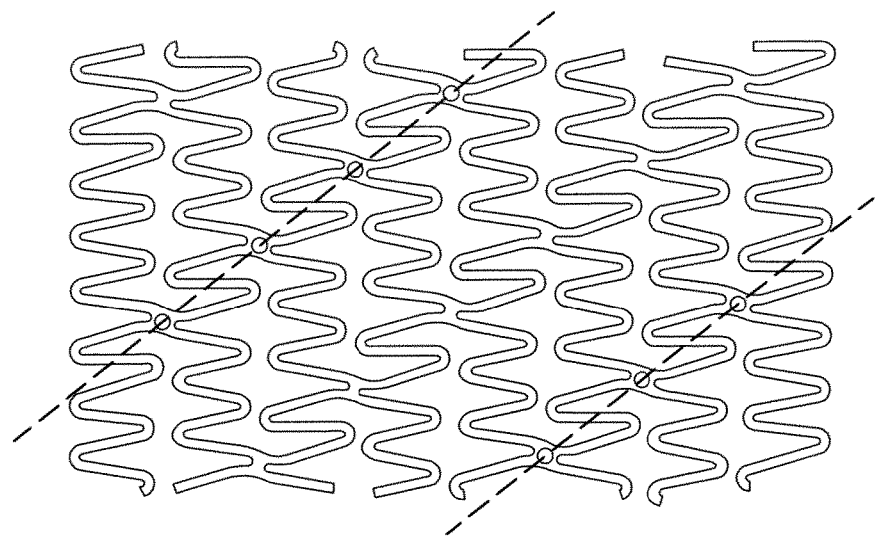
FIG. 5A and FIG. 5B illustrate a planar view of a stent material with radiopaque markers.
Figure 5B:
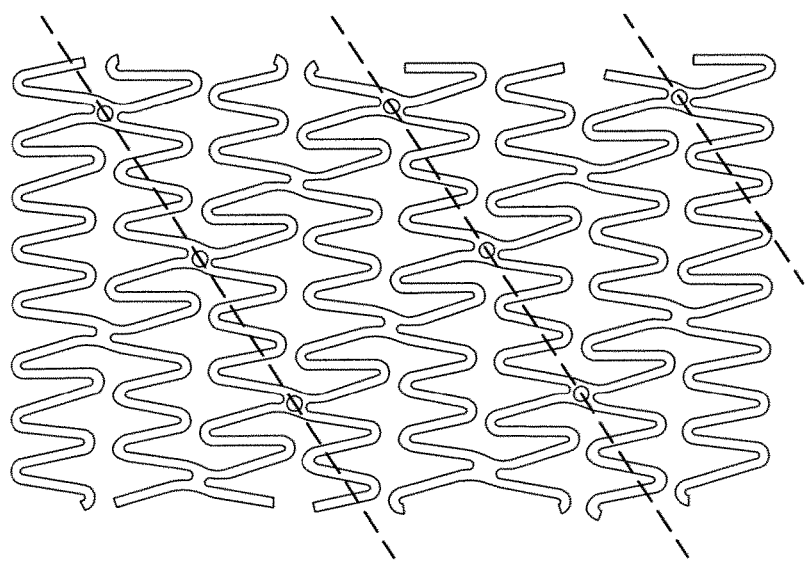

FIG. 5A and FIG. 5B illustrate a planar view of a stent material with radiopaque markers. As illustrated in FIGS. 5A and 5B the radiopaque markers can be aligned in the structure to allow for easier identification upon imaging or use of other detection methods.

Figure 6:
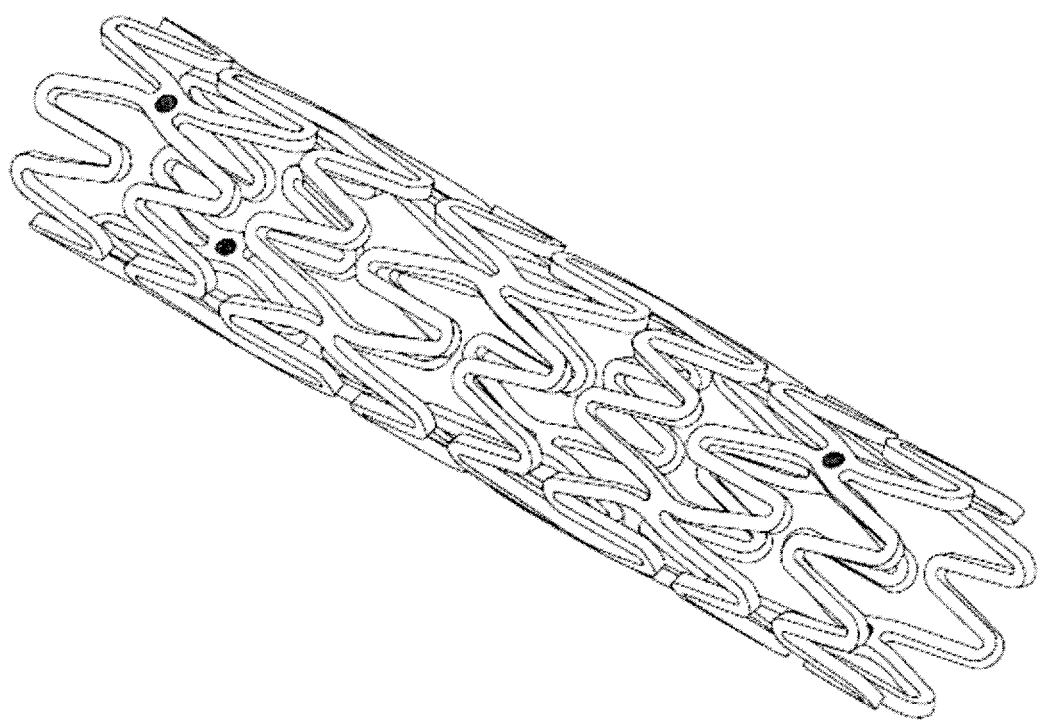
FIG. 6 shows an overview perspective of an actual stent with an embodiment radiopaque marker pattern, each located at a connection junction of the meandering strut.
Figure 7:
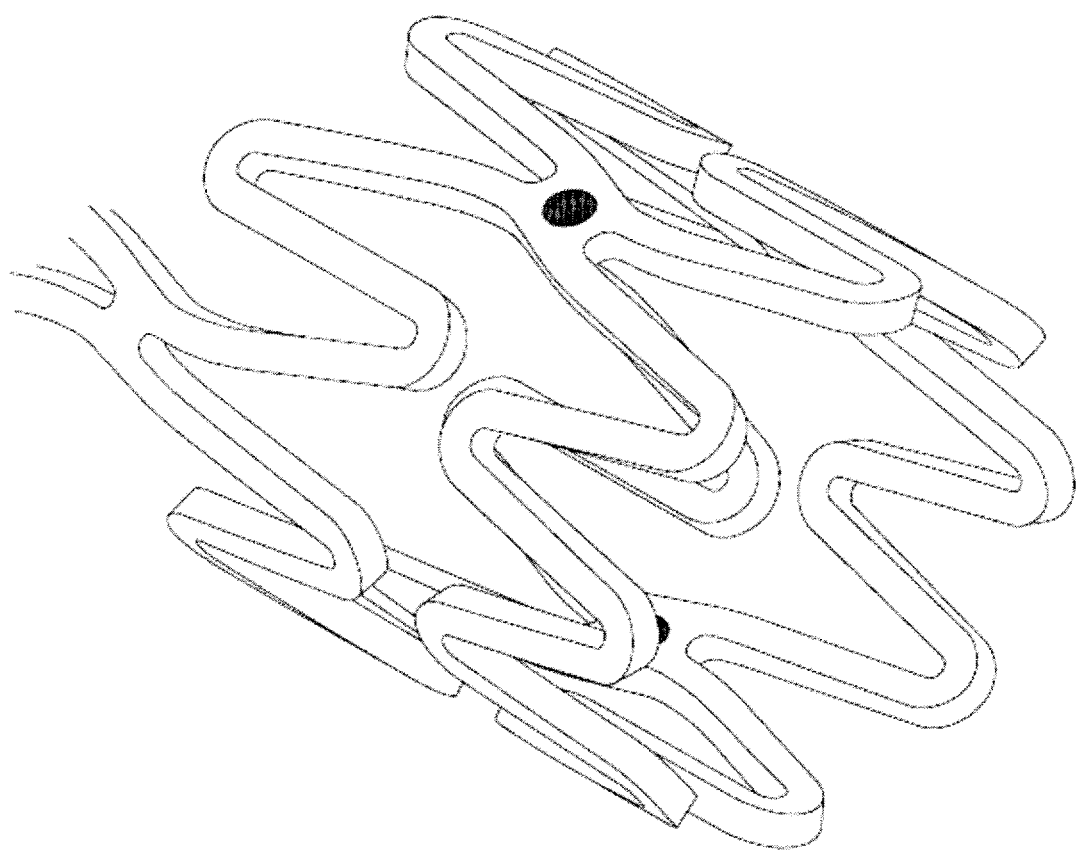
FIG. 7 shows a close-up view of a portion of the radiopaque marked stent of FIG. 6.

FIG. 6 shows an overview perspective of an actual stent with an embodiment radiopaque marker pattern, each located at a connection junction of the meandering strut. FIG. 7 shows a close-up view of a portion of the radiopaque marked stent of FIG. 6.

Figure 8:
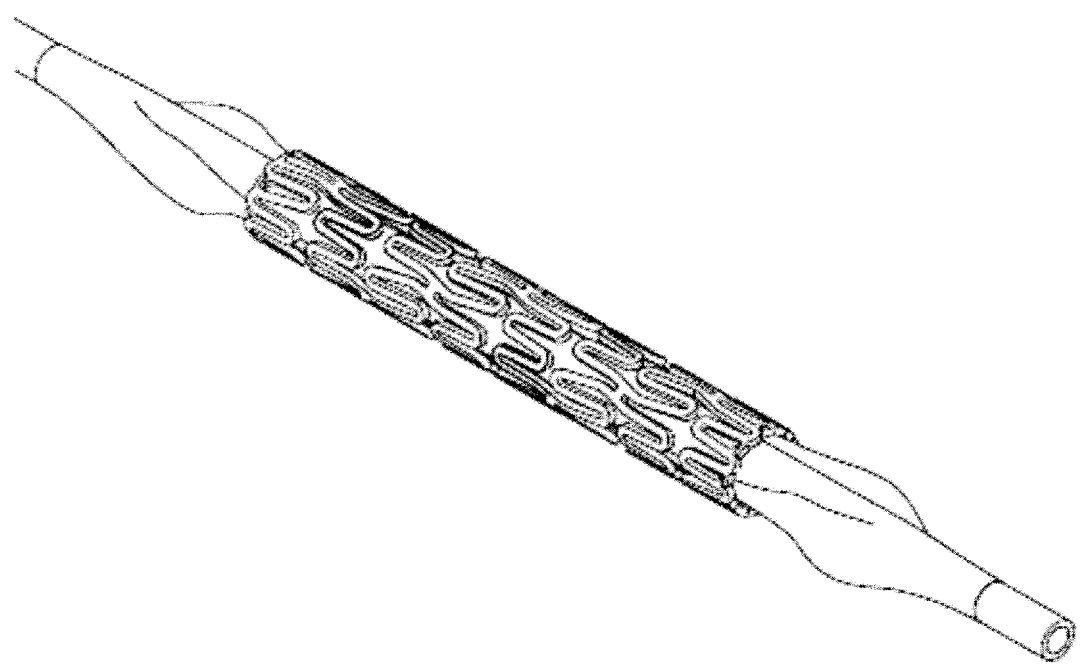
FIG. 8 shows in perspective view a stent embodiment of the present invention deployed on a balloon catheter.

FIG. 8 shows in perspective view a stent embodiment of the present invention deployed on a ballon catheter.

Figure 9:
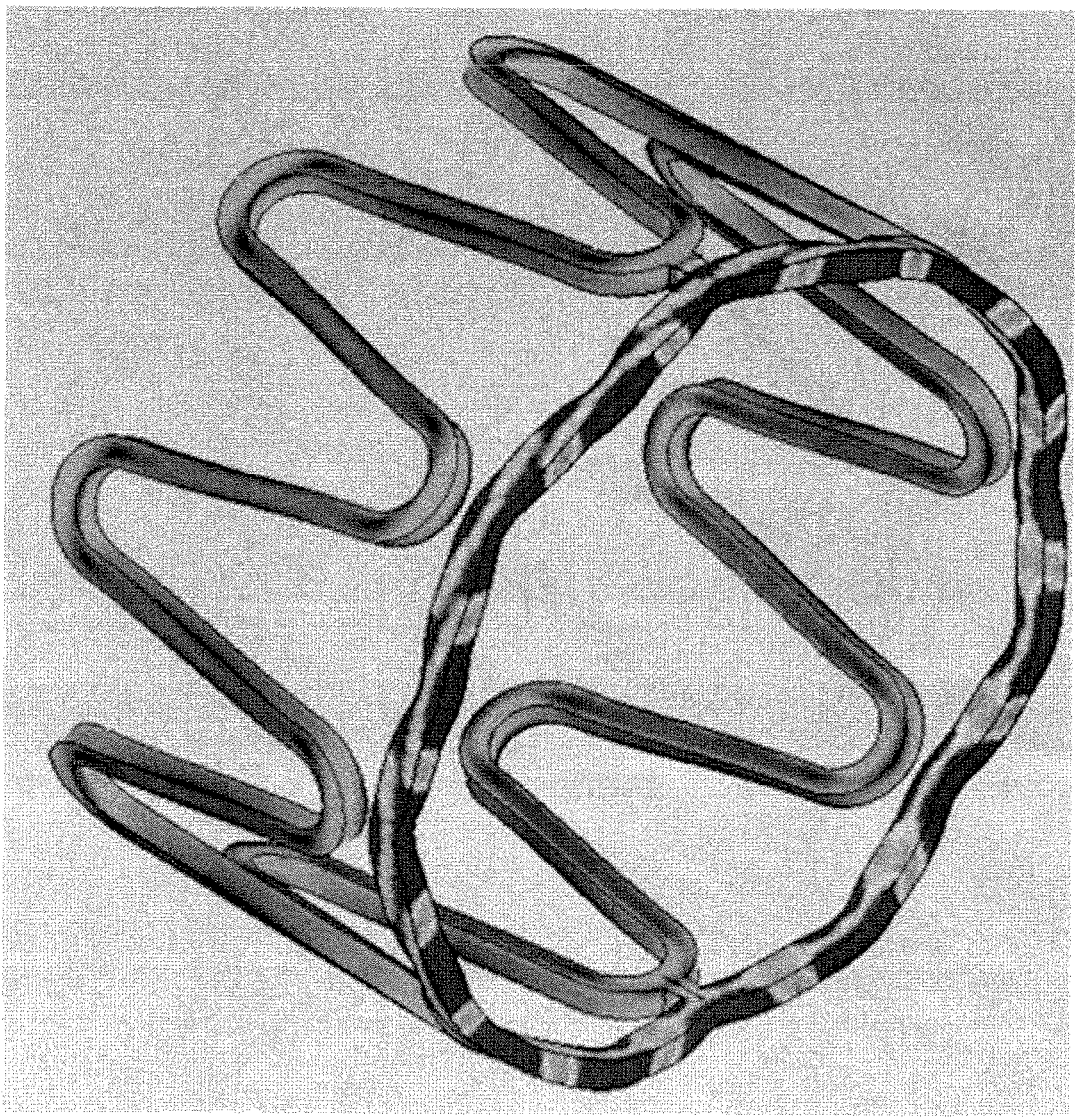
FIG. 9 depicts a fully expanded bioabsorbable scaffold stent comprising ring structuring showing fully crystallized holding rings or hoops.

FIG. 9 depicts a fully expanded bioabsorbable scaffold stent comprising ring structuring showing fully crystallized holding rings or hoops.

Figure 10A:
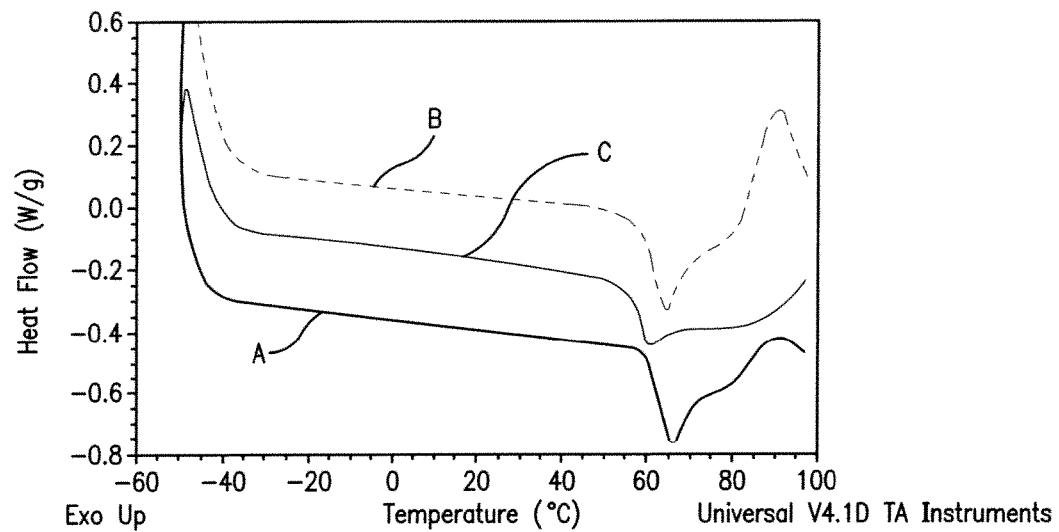
FIG. 10A and FIG. 10B illustrates DSC flow curves demonstrating single Tg and 10B shows a DSC flow curve showing double Tg.
Figure 10B:
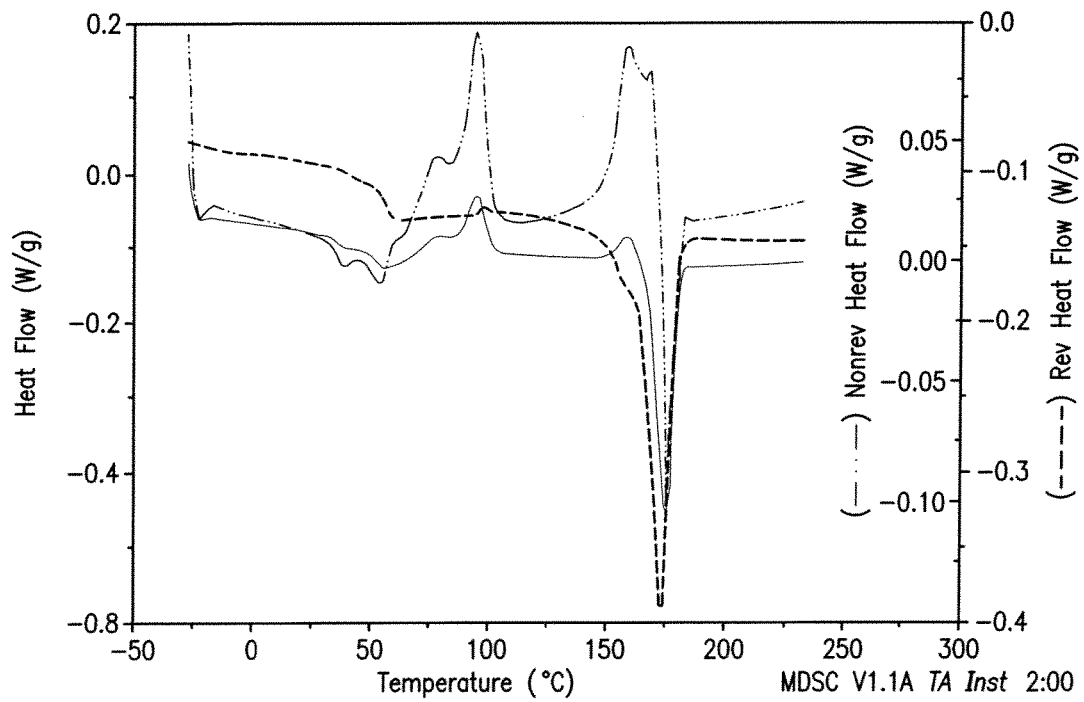

FIG. 10A and FIG. 10B illustrates DSC flow curves demonstrating single Tg and 10B shows a DSC flow curve showing double Tg.

Taking reference to FIG. 10A, polymer samples were analyzed for thermal transition temperatures using TA Instrument Q10 DSC. The samples were (A) Poly(L-co-DL-lactide) 70:30 copolymer, (B) Poly(L-lactide/Poly L-lactide-co-ϵ-caprolactone), and (C) Poly(L-lactide/Poly L-lactide-co-TMC). The polymers gave broad transition peaks at Tg's of 30° C. and 50° C., which were only present on the original run. Transition temperatures and curves of the later runs are given in the table below.

TABLE

| Polymer | Transition Temperature (C.) |
|---|---|
| PLDL 70/30 | 66 |
| LPLA/PCL Hybrid | 64 |
| LPLA/TMC | 61 |

Taking reference to FIG. 10B, other polymer samples (LPLA/TMC hybrid) were analyzed via DSC showing a double Tg.

What is claimed is:

1. A crystallized bioabsorbable polymer composition comprising poly (L-lactide) moiety, and/or a poly (D-lactide) moiety, and/or poly L-lactide-co-PEG moiety, and/or poly D-lactide-co-PEG moiety, linked or admixed with poly (L-lactide-co-Tri-methylene-carbonate) or poly (D-lactide-co-ϵ-caprolactone) or poly (L-lactide-co-ϵ-caprolactone) in the form of block copolymers or blocky random copolymers.

2. The composition of claim 1, comprising poly (L-lactide), linked or admixed with a modifying copolymer comprising, poly (L-lactide-co-ϵ-caprolactone) in the form of block copolymer or blocky random copolymer.

* * * * *